United States Patent
Heise et al.

(10) Patent No.: US 8,142,387 B2
(45) Date of Patent: Mar. 27, 2012

(54) TUBULAR VASCULAR TRANSPLANT

(76) Inventors: Michael Heise, Jena (DE); Christoph Heidenhain, Berliln (DE)

( * ) Notice: Subject to any disclaimer, the term of this patent is extended or adjusted under 35 U.S.C. 154(b) by 454 days.

(21) Appl. No.: 12/309,798

(22) PCT Filed: Jul. 20, 2007

(86) PCT No.: PCT/DE2007/001289
§ 371 (c)(1),
(2), (4) Date: Mar. 9, 2009

(87) PCT Pub. No.: WO2008/014752
PCT Pub. Date: Feb. 7, 2008

(65) Prior Publication Data
US 2009/0326431 A1    Dec. 31, 2009

(30) Foreign Application Priority Data
Aug. 2, 2006 (DE) .......................... 10 2006 036 073

(51) Int. Cl.
*A61M 5/00* (2006.01)
*A61F 2/06* (2006.01)
(52) U.S. Cl. ............................... 604/9; 604/8; 623/1.31
(58) Field of Classification Search ................ 604/8, 9, 604/264; 623/1.1, 1.29, 1.31
See application file for complete search history.

(56) References Cited

U.S. PATENT DOCUMENTS

| 4,503,568 A | * | 3/1985 | Madras ........................... 623/1.3 |
| 6,589,278 B1 | * | 7/2003 | Harris et al. .................. 623/1.31 |
| 7,553,316 B2 | * | 6/2009 | Scholz et al. .................. 606/153 |

FOREIGN PATENT DOCUMENTS
EP      1 011 521 B1    2/1996

OTHER PUBLICATIONS

Improved Patency of Prosthetic Arteriovenous Grafts with an Acute Anastomotic Angle and Flow Diffuser, Albert G. Hakain et al., Journal of Vascular Surgery, vol. 37, No. 5, pp. 1032-1035.

* cited by examiner

*Primary Examiner* — Leslie Deak
(74) *Attorney, Agent, or Firm* — Karl F. Milde, Jr.; Eckert Seamans Cherin & Mellott, LLC

(57) ABSTRACT

A tubular vascular transplant (1, 1', 1", 1''') serves for connecting vessels in the human body. The transplant, in particular made of expanded polytetrafluoroethylene (ePTFE), can preferably be used for an arteriovenous shunt for carrying out a dialysis. The transplant is connected by its first, proximal end to a vessel, for example an artery (2), and by its distal end to another location of the same vessel or to a different vessel, for example a vein (3). The lumen of the transplant (1, 1', 1", and 1''') widens in a steadily conical manner in the region of its distal end and forms a diffuser (8) there. The cone angle (a) of the wall of the diffuser (8) with respect to the central flow direction of the blood in the transplant (1', 1", 1''') is preferably 6° to 7°. In the region of the diffuser (8), preferably at least one, preferably planar, dividing wall (11, 11', 11a, and 11b) is provided, running in the central flow direction of the blood. This makes it possible to prevent the formation of an intimal hyperplasia and a pseudointima.

15 Claims, 3 Drawing Sheets

Straight PTFE-Portion | Diffusor-Portion

Straight PTFE-Portion | Diffusor-Portion

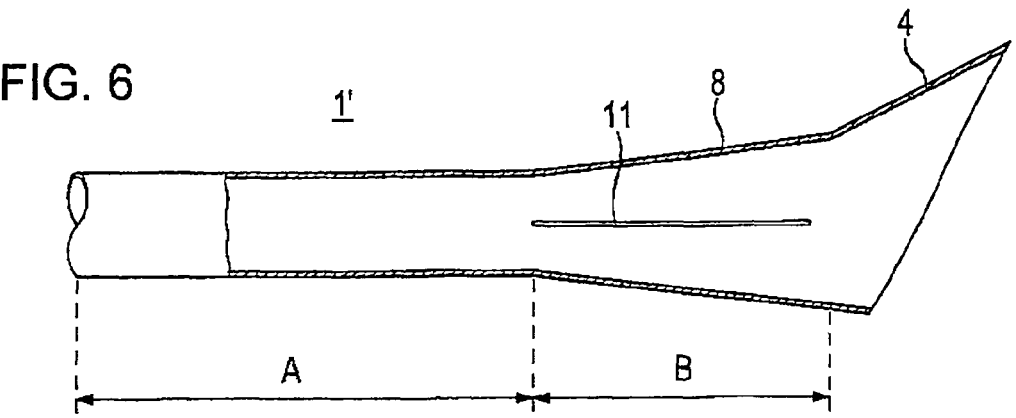
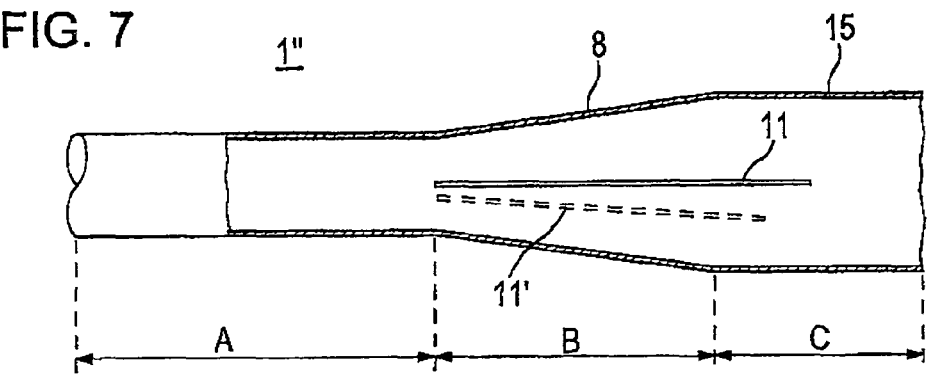
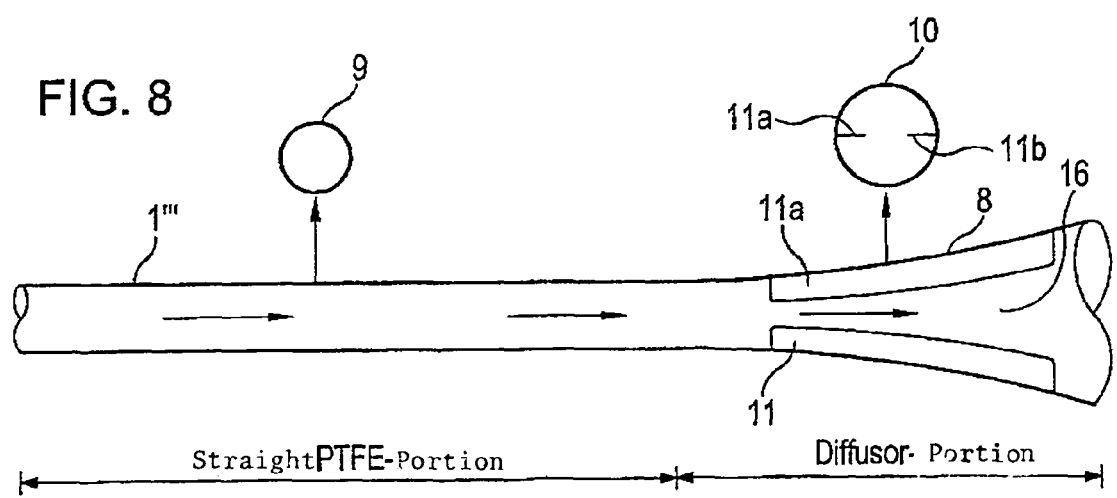

TUBULAR VASCULAR TRANSPLANT

BACKGROUND OF THE INVENTION

The invention refers to a tubular vascular transplant.

Such transplants are used to connect perfused blood vessels in the human body. The transplant is connected by its first proximal end to a vessel and by its second distal end to another location of the same vessel or a different vessel.

An example is the so called peripheral transplant which is used to bypass a non-perfused blood vessel with the aid of the transplant. Applications within an end-to-side-anastomosis are possible.

Another example of this type of tubular vascular transplant is an arteriovenous shunt. It is a parallel or bypass connection between an artery and a vein, usually in the upper or lower arm to enable operative vascular access during a dialysis. This type of shunt is used when the patient's own veins are inadequately developed to allow for an effective dialysis. Using an arteriovenous shunt, flow rates of up to 1000 milliliters per minute (1000 ml/min) are possible. During a dialysis, a first puncture needle is inserted into the transplant in the proximal area, thus, the area facing the artery. From there the blood will flow through the transplant via a dialysis machine and there it will flow back through a second puncture needle in the distal end of the designated transplant area.

Tubular vascular transplants are usually made of expanded polytetrafluoroethylene and are referred to as an ePTFE-Transplant.

A general problem with such tubular vascular transplants is the formation of a stenosis in the distal region of the transplant. This type of stenosis usually develops within the first six months to two years after the transplant has been carried out. With an arteriovenous shunt the stenosis develops in two areas of the anastomosis: At the base body of the receiving vein an intimal hyperplasia develops near the anastomosis. A pseudointima is formed in the distal end of the transplant.

Similar problems also arise with peripheral transplants or end-to-side-anastomosis.

These chronic changes are to be regarded as a forming phenomena independent from each other. The causes of both phenomena vary according to current scientific findings:

1. Intimal hyperplasia, for example on the base body of the vein with an arteriovenous shunt, is formed due to very high wall shear stress (WSS) in the wall region of the vein which is mainly caused by the angular penetration of the high speed central blood flow.
2. Pseudointimal hyperplasia in the transplant region is formed by dead water zones, so called separation zones, where the blood only flows very slowly or not at all.

Through the formation of parietal thrombosis a conversion of thrombus occurs in a pseudointima which ultimately leads to luminal narrowing in the transplant. The stenosis is very distinctive here due to widened dead water and vertebration zones in the widened anastomosis region.

The problem with stenosis, in particularly venous stenosis has been well-established for some time. The so called Venaflo®-Transplant has been developed for the arteriovenous shunt (see also EP 1 011 521 B1, in this case in particularly FIGS. 6A and 6B with related description). This European patent specification was also published as DE 696 34 278 T2. This well known transplant is widened by a flange in the distal region which causes a vertebration. The shear stress on the base body of the receiving vessel (i.e.: a vein) is reduced by the vertebrae which prevents a formation of intimal hyperplasia. Various studies show that the stenosis rate is actually less by using this famous Implant in comparison to regular straight end-to-side-transplants. On the other hand however, a distinct pseudointima can form in the distal region when using this famous transplant. This could be due to the development of particularly large vertebration and separation zones in the widening of the transplant.

In the Journal of Vascular Surgery, Volume 37, No. 5, May 2003, as of Page 1032, Albert G. Hakain et al. published a suggestion for the development of an arteriovenous shunt in the venous-side area of the anastomosis.

The straight ePTFE-Prosthesis was connected in such a way in the vein through special incisions, that a diffusion-type flow path was created in the venous area. If in addition the entry angle between the prosthesis and the vein is only small, in particularly around 15 degrees, the blood flow rates can be increased according to those studies. Turbulences are also prevented in this way. Furthermore only a slight stenosis formation showed after 24 months.

Please find below a discussion on the addressed problems of an arteriovenous shunt whereby these problems also occur similarly with peripheral vascular transplants.

SUMMARY OF THE INVENTION

In order to reduce the stenosis rate and improve the clinical effect, two aspects must be improved:
1. The extremely high wall shear stress (WSS) caused by the angular penetration of the central blood flow in the venous wall region must be significantly reduced.
2. The formation of separation zones within the transplant must be prevented, in particularly in the venous anastomosis region.

Thus, the invention must indicate a tubular vascular transplant as mentioned previously whereby the flow ratio particularly in the distal region of the transplant is controlled in such a way, that the formation of stenosis and with that the formation of an intimal hyperplasia and pseudointima can preferably or significantly be reduced.

This objective, as well as further objectives which will become apparent from the discussion that follows, are achieved, in accordance with the present invention, by providing a lumen of the transplant which consistently widens conically in the region of its distal end and forms a diffuser there.

The lumen of the transplant widens consistently conical accordingly in the distal end area and a diffuser is formed.

The blood flow speed can be cut off in a controlled manner and reduced by placing a diffuser into the distal area of the transplant when using an arteriovenous shunt in the venous part region of this shunt. Significantly reduced wall shear stress (WSS) of the receiving vessels (i.e.: a vein) can be achieved by slowing down the flow. The cone angle should be selected at less than 10°, preferably between 6° and 7°. Otherwise flow separation will reoccur and pseudointima will develop.

By placing a diffuser in the distal region of the transplant, the formation of an intimal hyperplasia on the base body of the receiving vessel as well as pseudointima in the distal region of the transplant can be avoided or significantly reduced.

In accordance with a preferred embodiment of the invention, at least one straight dividing wall is envisioned towards the blood central flow or preferably parallel to it that is designated between the wall regions located opposite to the diffuser. The blood flow will be divided into two halves through at least one of these longitudinal dividing walls in the diffuser region of the transplant. However, overall the diffuser effect is maintained.

Besides, it is quite possible to insert not just one dividing wall into the diffuser region, but several dividing walls. Or, if necessary even dividing walls that face each other. This is especially the case with extreme diffuser types.

It is also possible to design an uncontinuous dividing wall. One or two dividing walls can extend similar to a sail into the diffuser from at least one wall region of the transplant. If two dividing walls facing each other are envisioned, an opening can remain between the edges.

If a single dividing wall is placed into the diffuser region of the transplant with a conical opening angle of the diffuser of approx. 7°, it is very surprising that 25% to 30% higher flow quantities have been achieved. These results were confirmed by studies of silicon models of such a transplant. The silicon models in this case were examined in a model cycle that was moved by an artificial heart. At the same time measurements of the flow speed were conducted by laser which enables the calculation of shear stress readings. We can assume that these results come about because a flow distribution and simultaneously a laminarization of the flow occurs in the diffuser region due to the straight dividing wall (or, if necessary, through several dividing walls) without the formation of separation zones which lead to power loss. These are particularly unfavorable, especially with a pulsative flow and highly viscous fluids such as those in a beating heart and in human blood as they have to come through over and over again with each heart beat.

Furthermore it has been established that larger cone angles can also be applied in the diffuser region by inserting at least one dividing wall into the distal area of the transplant. However, for an arteriovenous shunt it appears to be ideal to use a diffuser with a cone angle of approx. 7° with an additional longitudinal dividing wall that achieves a hemodynamic optimal version.

For peripheral vascular transplants it could be beneficial that a distal end region or end tube connects to the diffuser region with primarily the same diameter corresponding to the diameter at the end of the diffuser region. The dividing wall should preferably reach at least partially into this end area.

For a full understanding of the present invention, reference should now be made to the following detailed description of the preferred embodiments of the invention as illustrated in the accompanying drawings.

BRIEF DESCRIPTION OF THE DRAWINGS

FIG. 6 is a partially sectioned diagram of an arteriovenous shunt of the type according to FIG. 3.

FIG. 7 is a partially sectioned diagram of a peripheral vascular transplant according to the invention.

FIG. 8 is a diagram of an additional embodiment example of an arteriovenous shunt according to the invention with a diffuser region and dividing walls envisioned for this area.

DESCRIPTION OF THE PREFERRED EMBODIMENTS

Figure 1:
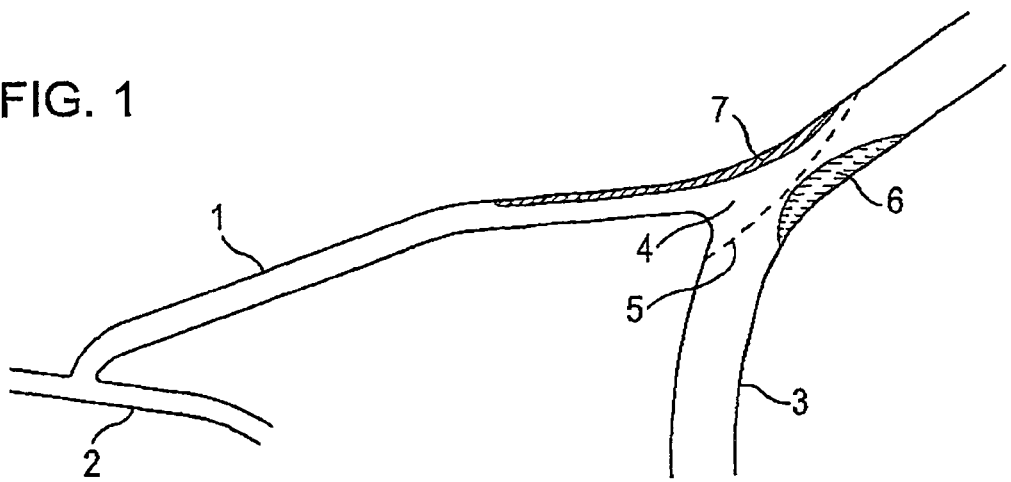
FIG. 1 is a tubular vascular transplant as an arteriovenous shunt according to the best available technology.

The preferred embodiments of the present invention will now be described with reference to FIGS. 1-8 of the drawings. Identical elements in the two figures are designated with the same reference numerals.

FIG. 1 shows an arteriovenous shunt that connects an artery 2 with a vein 3. Shunt 1 is a tubular vascular transplant made of ePTFE that diverts at its proximal end of the artery 2 and leads into vein 3 with primarily the same diameter whereby the connection between shunt 1 and the vein occurs via a flange 4. This is connected with vein 3 by a dash line suture 5. As explained previously, an intimal hyperplasia 6 is formed via an angular penetrated central blood flow at the base body of the vein which is released due to the high wall shear stress (WSS). Parallel to this pseudointimal hyperplasia 7 is formed in shunt 1 in the distal region which is primarily released by separation zones in the blood flow.

Figure 2:
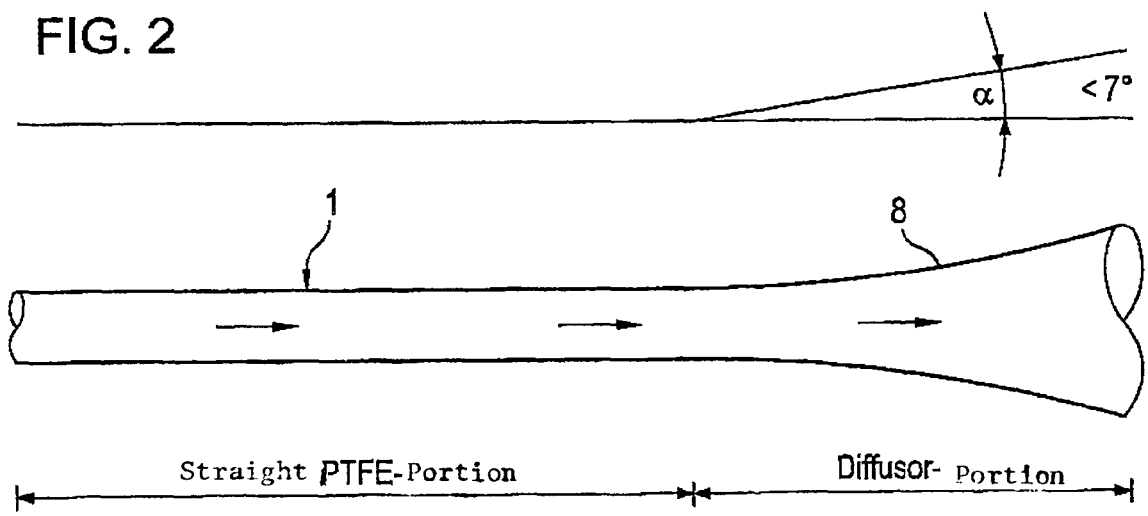
FIG. 2 is a schematic cross-section through part of an arteriovenous shunt with a distal diffuser region according to the invention.

FIG. 2 shows a schematic part of an arteriovenous shunt 1 according to the invention. Starting from the artery not shown here, this shunt 1 is a tube with a primarily consistent diameter that widens in the region facing the vein, similar to a conical diffuser 8 with a cone angle of approx. 6° to 7°.

A flange could be placed here if necessary, which is not shown in this illustration, in order to connect shunt 1 with the vein as shown in FIG. 1.

Figure 3:
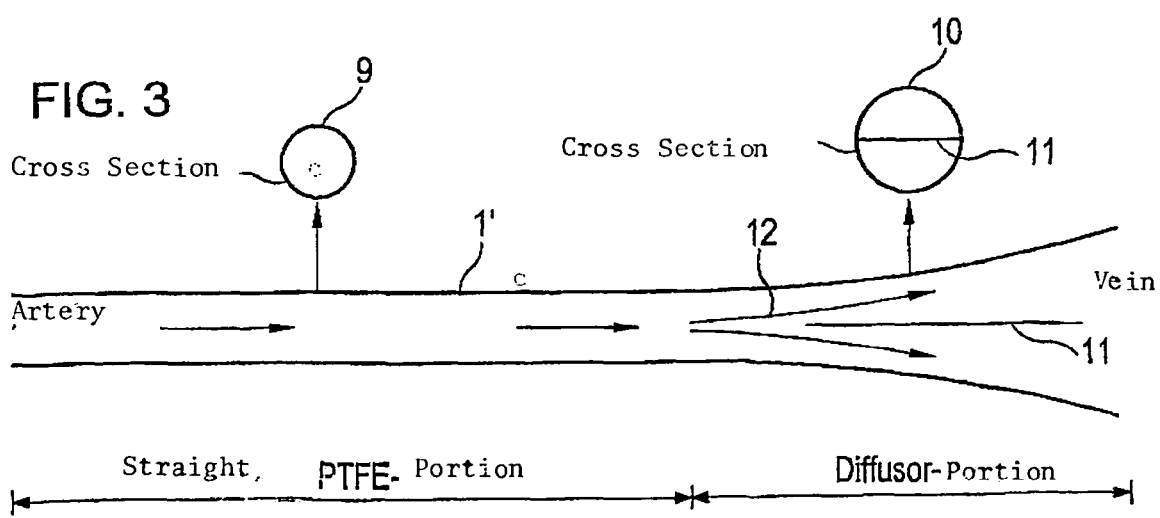
FIG. 3 is a diagram of an additional embodiment example of an arteriovenous shunt with a diffuser area according to the invention and one of the dividing walls envisioned for this region.

FIG. 3 shows a second embodiment of an arteriovenous shunt 1' that initially shows a primarily constant cross-section 9 starting out from the artery and subsequently as shown in FIG. 2 migrates into a diffuser 8, also with a marginal cone angle of 6° to 7°. The consistently enlarging cross-section of diffuser 8 is signified as 10. A straight dividing wall 11 is designated to this diffuser 8 which in this case runs through the middle of diffuser 8 and is connected with wall regions of diffuser 8 that are located on the opposite side. This is also shown in cross-section 10. As indicated by arrows 12, the blood flow is split open with dividing wall 11. The blood flow is a laminar flow in order to prevent formation of vertebrae or separation zones. In addition, the flow speed reduces due to the widening of diffuser 8, so that the wall shear stress (WSS) at the base body of vein 3 is significantly reduced. This prevents a formation of initmal hyperplasia at the base body of vein 3 as well as pseudointima in the shunt.

Figure 4:
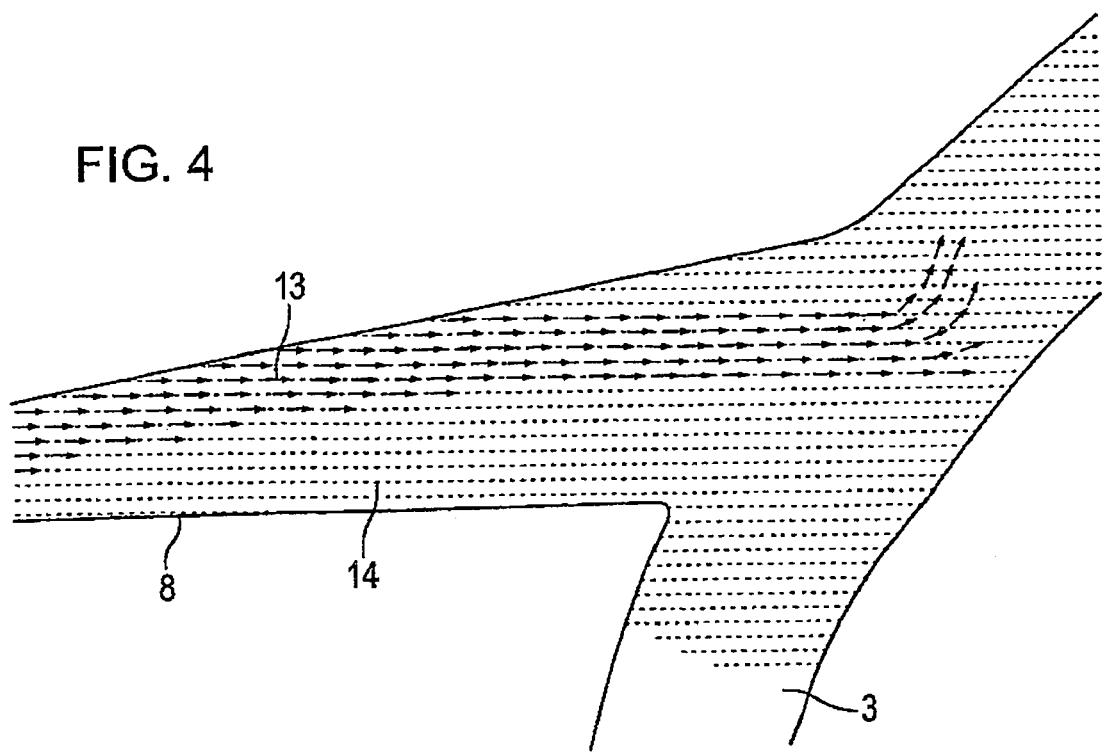
FIG. 4 is a flow diagram in the diffuser region for an arteriovenous shunt according to FIG. 2.

FIG. 4 shows a flow diagram (Particle Image Velocimetry) for a shunt according to FIG. 2. Illustrated here are only diffuser 8 of the shunt and a part of vein 3. FIG. 4 shows laminar flow areas which are signified by black short lines whilst slower flows are signified by dots. In FIG. 4 top half you can see that a stable laminar flow 13 is developing, whereas on the opposite side in FIG. 4 bottom half a certain separation zone 14 is still present. Simultaneously the shear stress at the base body of vein 3 is reduced due to the slowing down of the central blood flow, so that the formation of intimal hyperplasia in this region is also significantly reduced.

The formation of pesudointima inside the shunt 1 is also significantly reduced through the laminar flow.

Figure 5:
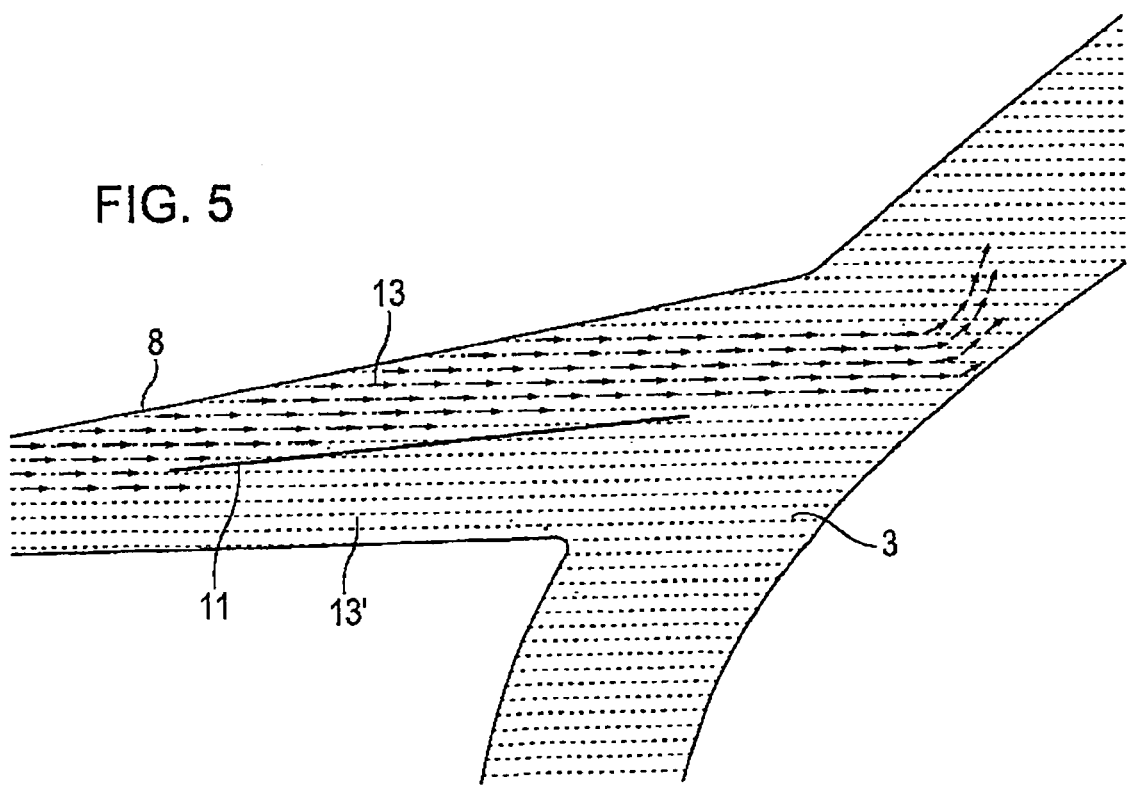
FIG. 5 is a flow diagram in the diffuser region for an arteriovenous shunt according to FIG. 3.

FIG. 5 shows a flow diagram for a shunt 1' according to FIG. 3 with a straight dividing wall 11. It is clearly visible that the central flow migrates to both sides of the dividing wall 11 in the laminar flow 13 or 13', so that separation zones practically do not occur in the flow 13' region. Likewise the wall shear stress (WSS) at the base body of vein 3 is reduced. A formation of intimal hyperplasia and pseudointima primarily does not occur or only marginally.

FIG. 6 shows a partial sectioned view of shunt 1' according to FIG. 3 with a straight dividing wall 11 in the diffuser 8 region whereby here a flange 4 is indicated to connect with the vein. In this case the cone angle of the diffuser is also 6° to 7° whereby higher readings are also possible due to the dividing wall 11. Also indicated are the "straight" region A of the shunt and the conical widened diffuser region B.

FIG. 7 shows a schematic vascular transplant 1" which is particularly suitable for peripheral transplants. Initially this transplant 1" shows a "straight" region A starting from its proximal end. Subsequently a diffuser area B with the conical widened diffuser 8 and finally in the distal area an additional "straight" region C connected to diffuser 8. Region C is formed through an end tube 15 that shows a diameter corresponding to the diameter at the end of diffuser 8.

A dividing wall 11 is also intended for this transplant 1" which reaches into the end tube 15 via the diffuser region B and at least partially to the second "straight" region C. Not illustrated here for this transplant is a flange connected to the end tube 15 for connecting to a receiving vessel, i.e.: through a suture.

Also indicated for this transplant 1" is a second straight dividing wall 11' which connects opposite lying wall regions of the shunt in the diffuser area B with the second "straight" region C. This additional dividing wall 11' can be designated inclined opposite dividing wall 11. However, other designs in accordance with requirements in terms of slowing down and laminarization of the flow are possible.

FIG. 8 is a diagram of another embodiment example of an arteriovenous Shunt 1''', similar to FIG. 3. On the other hand this shunt 1''' initially shows a primarily consistent cross-section 9 starting from the artery which consistently and conically enlarges in the diffuser 8 region and is signified as 10 in FIG. 8. Two sail-type dividing walls 11a and 11b are designated in diffuser 8 starting from two wall regions located on the opposite side. These reach into the diffuser whereby a conical widened opening 16 remains between the inside edges of the partitioned-dividing walls 11a and 11b. Applying this type of configuration can also prevent separation zones in the transplant as well as the formation of vertebrae. This significantly reduces wall shear stress (WSS) at the base body of the vein. There is no or only marginal development of intimal hyperplasia at the base body of the vein and no pseudointima in the shunt. Likewise, the diffuser effect is primarily maintained.

Other embodiments of the invention are possible even though primarily straight dividing walls have been described in the preceding paragraphs: For example—the surfaces of the dividing walls can be structured, i.e.: with microstructures using microbubbles in order to achieve a smooth flow without sticking to the dividing walls. Such microstructures, for example similar to a lotus effect or sharks skin, are already well-established in other technique areas.

There has thus been shown and described a novel tubular vascular transplant which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A tubular vascular transplant for the connection of blood vessels in the human body, the transplant having a wall forming a lumen and having a proximal end adapted to connect with a vessel and a distal end adapted to connect with one of (a) the same vessel at a different location and (b) another vessel; wherein the lumen of the transplant widens conically in the region of said distal end and forms a diffuser, and wherein the transplant includes a first dividing wall, disposed within said lumen in the diffuser region of the transplant and extending axially in a direction of blood flow within the lumen.

2. Transplant according to claim 1, wherein the conically widened the transplant wall in the region of the diffuser has a cone angle ($\alpha$) in relation to the direction of blood flow such that dead fluid or separation zones do not, or only marginally, occur in which blood only flows very slowly.

3. Implant according to claim 2, wherein the cone angle ($\alpha$) of the diffuser is less than 10°.

4. Transplant according to claim 3, wherein the cone angle ($\alpha$) of the diffuser is in the range of 6° to 7°.

5. Transplant according to claim 2, wherein the cone angle ($\alpha$) of the diffuser is between 5° and 15°.

6. Transplant according to claim 1, wherein the dividing wall is is fastened to one side of the transplant wall in the region of the diffuser.

7. Transplant according to claim 1, wherein the dividing wall is straight.

8. Transplant according to claim 1, wherein the dividing wall connects opposite sides of the transplant wall in the region of the diffuser.

9. Transplant according to claim 1, wherein the dividing wall extends partially into the diffuser from the transplant wall.

10. Transplant according to claim 9, wherein the dividing wall consists of two partial-dividing walls that reach into the diffuser from the transplant wall on opposite sides thereof, respectively, with an opening remaining between inside edges of the two partial-dividing walls.

11. Transplant according to claim 1, further comprising a second dividing wall in the diffuser region arranged parallel or inclined with respect to the first dividing wall.

12. Transplant according to claim 1, wherein a distal end region of a blood vessel with a primarily consistent diameter corresponding to the diameter at the end of the diffuser connects to the diffuser and wherein the dividing wall reaches at least partially into this end region.

13. Transplant according to claim 1, wherein the transplant wall is made of expanded polytetrafluoroethylene.

14. Transplant according to claim 1, which is configured as an arteriovenous shunt to carry out a dialysis.

15. Transplant according the claim 1, wherein the dividing wall is centrally located in the lumen.

* * * * *